(12) United States Patent
Fadgen et al.

(10) Patent No.: US 8,312,762 B2
(45) Date of Patent: Nov. 20, 2012

(54) DEVICE AND METHODS FOR REDUCING PRESSURE AND FLOW PERTURBATIONS IN A CHROMATOGRAPHIC SYSTEM

(75) Inventors: Keith Fadgen, Hope Valley, RI (US); James E. Usowicz, Webster, MA (US); Miguel Soares, Norton, MA (US)

(73) Assignee: Waters Technologies Corporation, Milford, MA (US)

( * ) Notice: Subject to any disclaimer, the term of this patent is extended or adjusted under 35 U.S.C. 154(b) by 760 days.

(21) Appl. No.: 12/282,895

(22) PCT Filed: Mar. 16, 2007

(86) PCT No.: PCT/US2007/064152
§ 371 (c)(1),
(2), (4) Date: Mar. 30, 2009

(87) PCT Pub. No.: WO2007/109529
PCT Pub. Date: Sep. 27, 2007

(65) Prior Publication Data
US 2010/0043539 A1   Feb. 25, 2010

Related U.S. Application Data

(60) Provisional application No. 60/783,347, filed on Mar. 17, 2006.

(51) Int. Cl.
*G01M 30/02* (2006.01)

(52) U.S. Cl. .................................. 73/61.55; 73/61.56
(58) Field of Classification Search ............... 73/61.55, 73/61.56
See application file for complete search history.

(56) References Cited

U.S. PATENT DOCUMENTS

| | | | |
|---|---|---|---|
| 5,699,665 A | 12/1997 | Coolidge et al. | |
| 5,701,933 A | 12/1997 | Lunzman et al. | |

FOREIGN PATENT DOCUMENTS

| | | |
|---|---|---|
| DE | 3943524 | 2/1991 |
| JP | 2003194790 | 9/2003 |
| JP | 2005201673 A | 7/2005 |
| WO | 2004025272 | 3/2004 |
| WO | 2006/023828 | 3/2006 |
| WO | WO 2006/023828 * | 3/2006 |

OTHER PUBLICATIONS

Cf Form 1507, EP, Dec. 10, 2010, European Search Report.
Translation of Notice of Rejection (Offical Action) for Japanese Application No. 2009-500623, dated Aug. 5, 2011.
Second Office Action in counterpart Japanese patent application No. 2009-500623, mailed Mar. 13, 2012; 7 pages.

* cited by examiner

*Primary Examiner* — Daniel Larkin
(74) *Attorney, Agent, or Firm* — Guerin & Rodriguez, LLP

(57) ABSTRACT

Embodiments of the present invention are directed to methods and apparatus for placing a sample in a chromatographic system. The device and method feature placing samples held in a sample loop to pressurization prior to placing such sample loop in communication with high pressure conduits.

28 Claims, 2 Drawing Sheets

DEVICE AND METHODS FOR REDUCING PRESSURE AND FLOW PERTURBATIONS IN A CHROMATOGRAPHIC SYSTEM

CROSS REFERENCE TO RELATED APPLICATIONS

This application is the National Stage of International Application No. PCT/US2007/064152, filed Mar. 16, 2007 and designating the United States, which claims benefit of a priority from U.S. Provisional Patent Application No. 60/783,347, filed Mar. 17, 2006. The entire contents of these applications are incorporated herein by reference.

STATEMENT REGARDING FEDERAL FUNDING

The present invention was made without Federal funding or sponsorship.

FIELD OF THE INVENTION

The present invention relates to instrumentation for performing chromatography.

BACKGROUND OF THE INVENTION

Embodiments of the present invention are directed to apparatus and methods for reducing pressure and flow perturbations in fluid conduits. As used herein the term "pressure and flow perturbations" refer to rapid changes in the movement of fluid in a conduit or rapid changes in the pressure of fluid in a conduit. These flow and pressure perturbations may compromise "sample integrity". As used herein, the term "sample integrity" refers to the desired composition of the sample. The boundaries of the sample become less sharp or distinct.

Aspects of the present invention are particularly useful in the field of chromatography. Chromatography is a chemical process in which compositions in solution (solutes) are separated from each other as the solution moves through a stationary material or phase. The compositions separate from each other based on the different affinity each composition has for the stationary phase. The solutions may comprise any fluid, such as, liquids, gases, supercritical fluids or mixtures thereof.

Chromatography is used to identify and quantify compositions held in a sample. The term "sample" is used herein to refer to any material that one desires to analyze.

High performance liquid chromatography, or HPLC, is a form of chromatography performed under pressure. The stationary phase is held in a column. A typical HPLC instrument may comprise a pump, conduits, sample injector, one or more columns and a detector. The solution is pumped through a conduit to a sample injector. At the sample injector, a sample is added to the solution in the conduit and conveyed to the column and through the stationary phase. Compositions in the solution separate as they traverse the stationary media in the column. The separated compositions are detected by a detector downstream of the column.

A typical HPLC instrument may operate at system pressures exceeding five thousand pounds per square inch (PSI). The term "system pressure" refers to the pressure in which the column operates. Recently, instruments have been introduced into the marketplace capable of operation at fifteen thousand PSI. Although the term HPLC refers to liquid, the principles of HPLC, for the purpose of this invention, apply equally to gases or supercritical fluids. Therefore, this document will use the term HPLC to refer to liquid, gas or supercritical fluid chromatography operating at pressures of up to five thousand PSI and up to and including extreme pressures of fifteen thousand PSI and above.

As used herein, the term "conduit" refers to pipes, tubes, capillaries, microfluidic channels, and the like.

The term "valve" refers to means to control, redirect, restrict or stop flow. The term "valve means" means one or more valves or moving a conduit to communicate with a different element of the instrument. For example, without limitation, sample injectors are often equipped with needles which are placed in fluid communication with vials containing sample and are able to move to different vials, solutions and other instrument stations. The term "sample injector" refers to a form of valve and conduits used to bring a section of conduit holding a sample into fluid communication with conduits upstream of a column. Sample injectors normally comprise multiport valves and a loop of conduit for holding a sample, needles and syringe pumps for withdrawing samples.

The term "column" refers to columns, cartridges, capillaries and the like for performing separations of a chromatographic nature. Columns are typically packed or loaded with a stationary phase. This stationary phase can be particulate or beadlike or a porous monolith or a substantially inert material. For the purpose of the present invention, the term "column" also refers to capillaries which are not packed or loaded with a stationary phase but rely on the surface area of the inner capillary wall to effect separations.

Solutions used in chromatography may take many forms and it is not unusual for the composition of the solution to change over the course of a separation. For example, it is often desirable to release components of a sample held on a stationary phase. By changing the composition of a solution flowing through the stationary phase, the components of the sample can be released. It is desirable to control the composition of the mixture such that the components of the sample are released in a reproducible manner.

It is difficult to maintain the integrity of a fluid sample in a conduit as flow is interrupted or the fluid experiences pressure disturbances.

SUMMARY OF THE INVENTION

Embodiments of the present invention are directed to methods and devices for placing a sample in a chromatography system having a system pressure. One embodiment of the invention directed to a device comprises a valve means, a sample introduction line, a withdrawal line, a sample loop, a column line, a constant flow line, a withdrawal pump, a pressure source, and control means.

The valve means is for selectively placing sample in a column line. The valve means comprises a sample port, withdrawing port, first loop port, second loop port, column port and constant flow port. The valve means has a plurality of positions comprising a first position, second position and third position. In the first position, one of the first loop port and the second loop port is in communication with the sample port and the remaining first loop port and second loop port is in communication with the withdrawal port. And, in the first position, the constant flow port is in communication with the column port. In the second position, at least one of the first loop port and the second loop port is in fluid communication with a pressure source. And, in the third position, the first loop port and said second loop port are in fluid communication with the constant flow port and the column port. The valve means in signal communication with control means and assumes the first position upon receiving a first signal command, assuming the second position upon receiving a second signal command and assuming the third position upon receiving a third signal command.

The sample introduction line is in fluid communication with the sample port and with a source of sample, and, upon the valve means assuming a second position, a source of pressure. The sample introduction line is for receiving sample and conveying the sample into the valve means and through at least one of the first sample port and second sample port and into the sample loop when the valve means is in the first position. And, the sample introduction line pressurizes the sample in the sample loop upon the valve means assuming the second position.

The withdrawal line is in fluid communication with the withdrawal port and a source of reduced pressure to withdraw sample through the sample introduction line and into valve means and the sample loop upon the valve means assuming the first position. The sample loop is in fluid communication with the first sample port and the second sample port for receiving sample withdrawn through the valve means and holding the sample. And, upon the valve means assuming the second position, pressurizing the sample. And, upon the valve means assuming a third position, discharging the sample through the valve means and the column port as the sample loop is placed in communication with the constant flow port and the column port.

The column line is in fluid communication with the column port for receiving sample from the sample loop and for directing sample to one or more columns. The constant flow line is for being placed in communication with a source of solvent.

The withdrawal pump is in fluid communication with the withdrawal line and in signal communication with control means. The withdrawal pump depressurizes the withdrawal line to pull sample into the sample introduction line when the valve means is in the first position. The pressure source is in fluid communication with at least one of the sample introduction line and the sample loop for placing the sample, held in the sample loop, under pressure.

The control means is in signal communication with the pressure source, the withdrawal pump and the valve means. The control means instructs by issuing a first command signal to the valve means to assume the first position in which a sample is received in the sample introduction line. The control means issues a second command signal to the valve means to assume the second position and signaling the pressure source to pressurize the sample loop while the sample is received therein to 70 to 100% of the system pressure to reduce pressure perturbations as the valve means moves to the third position.

Embodiments of the present device are particularly useful to reduce flow and pressure perturbations in sample having trailing end and lead fronts in which an air bubble is placed to provide definition to the sample. The air bubbles allow the fluid to change volumes when the pressures are not matched and contribute to pressure and flow perturbations.

The term "control means" refers to computer processing units (CPUs), microprocessors, mainframe computers, and personal computers. Computers and CPUs can be integrated in the device or communicate via networks. As used herein, the term "signal communicate" refers to electro-magnetic communication by wire, or wireless radio-wave, optics, and the like. In contrast, the term "fluid communication" refers to plumbed together or capable of exchanging fluids.

The pressure source is placed in fluid communication with the sample introduction line or with the sample loop during pressurization. The pressure source may comprise a pump or a source of compressed fluid. One embodiment of the pressure source is a valve in fluid communication with a pressure source. A further embodiment of the pressure source is sample introduction line having a needle capable of being placed in communication with a pressure source. The needle is used to descend into a sample vial and is moved robotically to a pressure source to which such needle is placed in fluid communication.

Thus, the needle has two positions. In one position, the needle is placed in a sample vial and upon the withdrawal pump depressurizing the sample introduction line, sample is drawn up into such line and into the sample loop. In the second position, needle is placed in fluid communication with a pressure source to pressurize the sample and fluids in the sample loop. Embodiments of the present invention preferably place the sample under pressure in said sample loop under static conditions.

A preferred sample loop has a volume in the range of 0.5 microliter to 50 microliters. A preferred sample has a volume of 0.1 to 45 microliters. The sample has a pre-compression volume prior to pressurization and a post compression volume after pressurization. A preferred post compression volume is 85 to 95% of the pre-compression volume.

A preferred pressure source comprises a pump such as a syringe pump that change volume at the rate of approximately 10 to 800 microliter per minute.

One embodiment of the present invention is in the nature of a sample injector to be placed in communication with a chromatography pump via the pump line. A further embodiment of the present invention is incorporated with a pump as part of an integrated chromatography system.

Embodiments of the present invention are used with a column. The column is placed in fluid communication with the column line. One embodiments of the present invention further comprises a detector. The detector is in fluid communication with the column. As used herein, the term "detector" refers to optical detectors such as absorbance detectors, fluorescence detectors, light scattering detectors, light refraction detectors, electromagnetic detectors, mass detectors, such as mass spectrometers and the like.

A further embodiment of the present invention features a method of a placing a sample in a chromatography system having a system pressure, comprising the steps of providing a device having a valve means, a sample introduction line, a withdrawal line, a sample loop, a column line, a constant flow line a withdrawal pump, a pressure source, and a control means, as previously described; and operating the device to place sample in the sample loop under pressure from said pressure source at 70% to 100% of the system pressure to reduce pressure perturbations.

Thus, embodiments of the present invention are directed to maintaining sample integrity, and improving chromatographic results, particularly with detectors that may be sensitive to pressure and flow perturbations. These and other features and advantages will be apparent to those skilled in the art upon viewing the Figures, briefly described hereinafter, and reading the detailed description of the invention that follows.

DETAILED DESCRIPTION OF THE INVENTION

Embodiments of the present invention will be described in detail as methods and devices for placing a sample in a chromatography system having a system pressure, with the understanding that embodiments of the present invention have application in other systems as well. The description that follows is a preferred embodiment which can be modified and altered to individual needs and desires without departing from the teaching herein.

Figure 1:
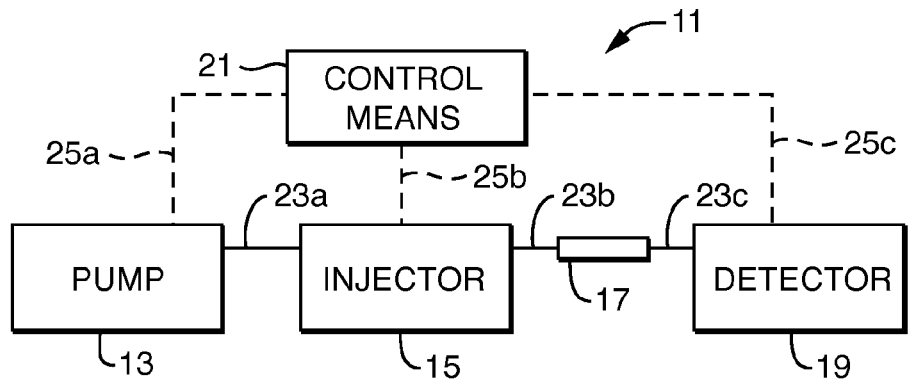
FIG. 1 is a schematic representation of a device embodying features of the present invention.

A chromatography system, generally designated by the numeral 11, is depicted in FIG. 1. The chromatography system comprises the following major elements: a pump 13, a sample injector 15, a column 17, a detector 19 and control means 21. The pump 13, sample injector 15, column 17 and detector 19 are in fluid communication by means of conduits 23a, 23b, and 23c respectively. The control means 21 is in signal communication with the pump 13, sample injector 15 and detector 19 by wires 25a, 25b, and 25c. Those skilled in the art will recognize that wires 25a, 25b and 25c represent one or more wires in the nature of a network or bundle. The control means 21 may also be in signal communication with the column 17, however, wires are not shown for purposes of simplification and clarity.

Wires 25a, 25b, and 25c, and all wires referred to in this paper represent communication by all means. Such wires 25a, 25b, and 25c represent wireless communication by infrared and radio transmissions, optical communication by fiberoptic cables and other information transmission means.

Control means 21 is a computer, CPU, microprocessor, mainframe computer or personal computer. Such computers are well known in the art and are available from numerous vendors such as Apple Corporation (Cupertino, Calif., U.S.A.) or Dell Computer Corporation (Round Rock, Tex., U.S.A.). CPUs and microprocessors are available from numerous vendors including Intel Corporation (Santa Clara, Calif., USA), AMD Corporation (Sunnyvale, Calif., U.S.A. and Freescale (Austin, Tex., U.S.A.).

Control means 21 operates with software or firmware. Software for performing chromatography and controlling chromatography instruments is available from several vendors, such as EMPOWER™ software from Waters Corporation (Milford, Mass., U.S.A.) or CHEMSTATION® software from Agilent Corporation (Waldbronn, Germany).

Pump 13 is a chromatography pump which are available from several vendors such as the ALLIANCE® series pumps and ACQUITY series pumps available from Waters Corporation (Milord, Mass., U.S.A.) or 1100® series pumps from Agilent Corporation (Waldbronn, Germany).

Column 17 is a chromatography column, column cartridge, or capillary known in the art. Such columns and capillaries are available from numerous vendors such as Waters Corporation (Milford, Mass., U.S.A.) and Phenomenex (Torrance, Calif., U.S.A.). Embodiments of the present invention have particular application for small scale chromatography using capillaries, small columns and microfluidics.

Detector 19 is an analytical detector of an optical, electrochemical or mass type. Typical optical detectors comprise absorbance detectors, Ramon detectors, fluorescence or chemiluminescence detectors, light scattering detectors, and the like, Typical mass type detectors are mass spectrometers. All such detectors are available from several sources including Waters Corporation (Milford, Mass., U.S.A.), Agilent Corporation (Waldbronn, Germany), Thermo Electron Corporation (Waltham, Mass., U.S.A.).

Sample injector 15 is a sample processing instrument known in the art and available from several venders including Waters Corporation (Milford, Mass., U.S.A.), Agilent Corporation (Waldbronn, Germany), Thermo Electron Corporation (Waltham, Mass., U.S.A.). Embodiments of the present invention share features with sample injectors such as the sample injector 15 depicted in FIG. 1 and this paper will carry the numeric designation 15 to such embodiments in the discussion that follows. Those skilled in the art will recognize that several components of the chromatography system 11 can be combined into and integrated single instrument rather than separate modules or components.

Figure 2:
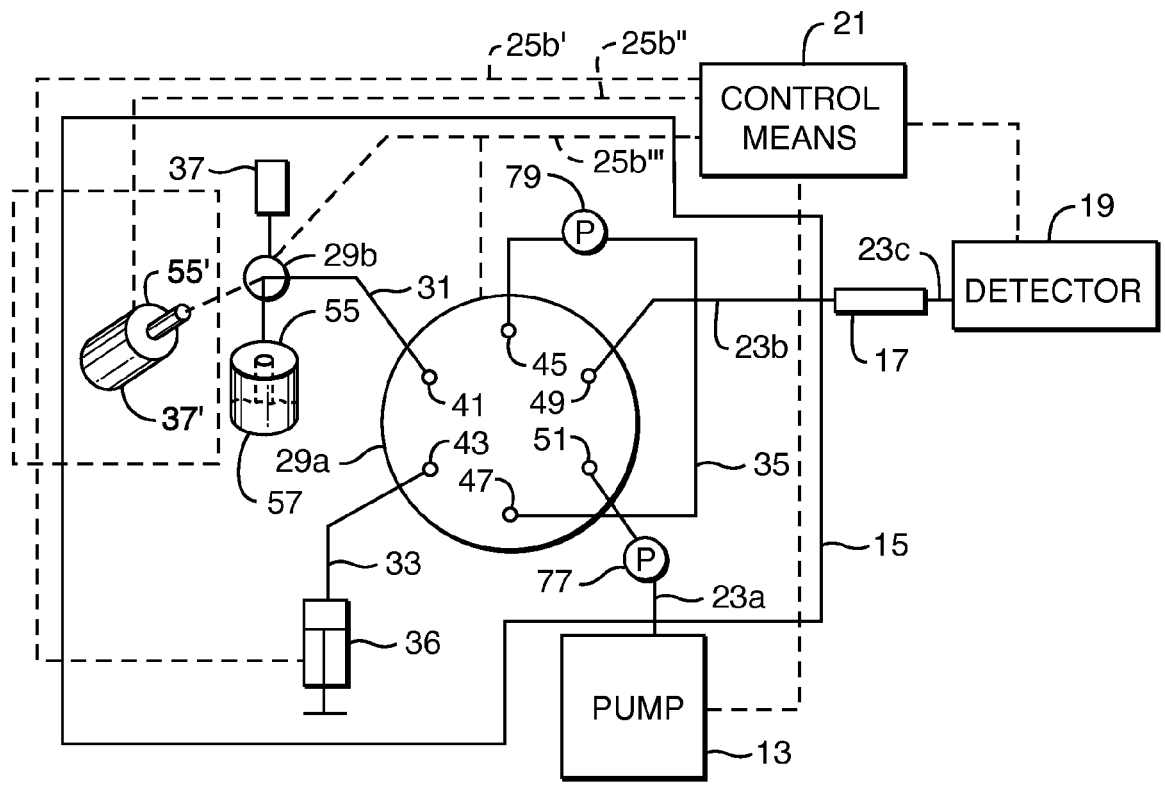
FIG. 2 is a schematic representation of a device embodying features of the present invention; and, FIG. 3 depicts a sample loop in cross section showing compressed and pre-compressed volumes.

The sample injection device 15 embodying features of the present invention is depicted in FIG. 2 with the major elements; a pump 13, a column 17, a detector 19 and control means 21. The pump 13, sample injector 15, column 17 and detector 19 are in fluid communication by means of conduits 23a, 23b, and 23c respectively. The control means 21 is in signal communication with the pump 13, and detector 19 by wires 25a, and 25c and with sample injector via wires 25b', 25b" and 25b''', the purpose of which will be described in greater detail later.

The sample injection device 15 comprises the following major elements: a valve means 29a, 29b, and 55' a sample introduction line 31, a withdrawal line 33, a sample loop 35, a column line which has been previously designated as 23b, a constant flow line which has been previously designated as 23a, a withdrawal pump 36, a pressure source 37.

The valve means 29a, 29b and 55' is for selectively placing sample in a column line 23b. Valve means 29a, 29b and 55' is comprised of a first valve 29a and a second valve 29b or needle positioning means represented generally by the numeral 55', which will be described in greater detail later.

The first valve 29a is in the nature of a multi-port valve of which six are depicted. Such mutiport valves are available from several venders such as Valco (Houston, Tex., U.S.A.) and Rheodyne (Rohnert Park, Calif., U.S.A.).

First valve 29a has a sample port 41, withdrawing port 43, first loop port 45, second loop port 47, column port 49 and constant flow port 51. The first valve 29a has a plurality of positions comprising a first position and third position. A second position will be described with respect to the second valve 29b and needle positioning means 55'.

The sample introduction line 31 is for receiving sample and conveying the sample into the valve means 29a, 29b, and 55' and through at least one of the first sample port 45 and second sample port 47 and into the sample loop 35 when the first valve 29a is in the first position. And, the sample introduction line 31 pressurizes the sample in the sample loop 35 upon the second valve 29b assuming the second position.

The withdrawal line 33 is in fluid communication with the withdrawal port 43 and a source of reduced pressure 36 to withdraw sample through the sample introduction line 31 and into valve means 29a and 29b and the sample loop 35 upon the valve means assuming the first position.

The source of reduced pressure 36 can be a vacuum line [not shown] with suitable valves [not shown] or, as depicted, a withdrawal pump. Withdrawal pump 36 is a syringe pump and is in fluid communication with the withdrawal line 33. Withdrawal pump 36, or a suitable valve connected to a vacuum source [not shown], are in signal communication with control means 21. The withdrawal pump 36 depressurizes the withdrawal line 33 to pull sample into the sample introduction line 31 when the first valve 29a is in the first position.

Figure 3:
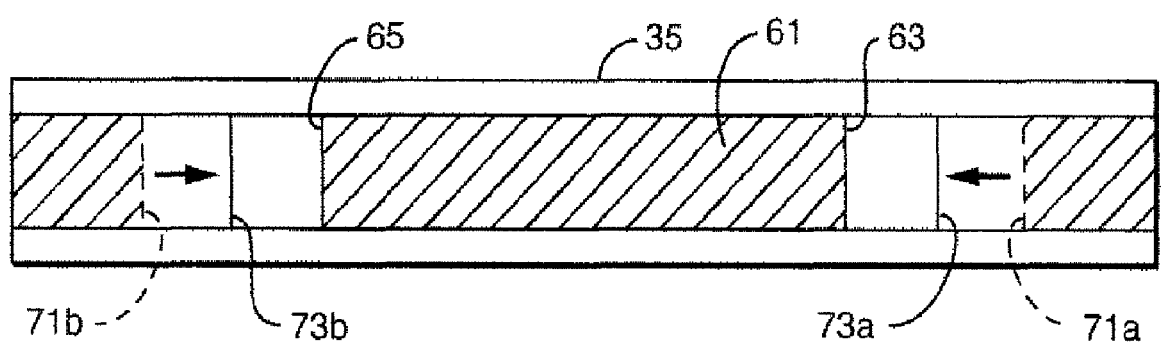

The sample loop 35 is in fluid communication with the first sample port 45 and the second sample port 47 for receiving sample withdrawn through the valve means 29a and 29b and holding the sample. The sample loop 35 has a volume of approximately 0.5 to 50 microliters. Turning now to FIG. 3, a sample loop 35 is depicted containing a sample 61. The sample 61 is withdrawn into the sample loop with a leading front 63 and a trailing end 65. A front bubble 67 and a back bubble 69 separate the sample 65 from solvent or preceding or following samples 71a and 71b. A sample 65 has a volume of 0.01 to 45 microliters.

The front bubble 67 and back bubble 69 preserve sample integrity and isolation. However, the front bubble 67 and back bubble 69 are placed in sample loop 35 under relatively low pressure with a volume of 0.1 to 3.0 microliters. The gaseous nature of the front bubble 67 and back bubble 69 makes the bubbles compressible. A sudden increase in pressure causes a sudden compression of the front bubble 67 and back bubble 69 moving the solvent or preceding or following samples inward to new compressed positions 73a and 73b. This sudden increase in pressure will result as the first valve 29a assumes a third position as best seen in FIG. 2. In the third position, the sample 61 is discharged through the first valve 29a and through column port 49 as the sample loop 35 is placed in communication with the constant flow port 51. The constant flow port 51 is in communication with pump 13 and has a pressure of 15,000 PSI or greater.

A sudden increase in pressure in sample loop 35 causes pressure and flow perturbations that can be detrimental to sample integrity and downstream components such as column 17 and detector 19. The pressure and flow perturbations are also a source of deviation in chromatographic results.

The pressure source 37 is in fluid communication with at least one of the sample introduction line 31 and the sample loop 35 for placing the sample, held in the sample loop 35, under pressure via second valve or needle movement means 29b. And, upon the valve means 29a and 29b assuming the second position, pressurizing the sample. This pressurization is preferably ramped to avoid sudden changes in the volumes of the front bubble 67 and back bubble 69. The ramp can be quite short from one to 90 seconds. This controlled movement of the solvent or preceding or following samples inward to new compressed positions 73a and 73b preserves sample integrity. The pressure source 37, as depicted is a syringe pump but may be other pumps or sources of compressed fluids. In the event the pump 13 and column 17 have a higher operating pressure then can be attained by the pressure source 37, the control means 21 sends a command to the pump 13 to reduce pumping to lower the operating pressure to correspond to the pressure source 37.

The column line 23b is in fluid communication with the column port 49 for receiving sample from the sample loop 35 and for directing sample to one or more columns 17. The column 17 is in fluid communication with the detector 19 via line 23c.

The constant flow line 23a is for being placed in communication with a source of solvent such as pump 13 with suitable solvent reservoirs [not shown]. Pump 13 has an operation pressure of up to and even exceeding 15,000 PSI. Preferably, the constant flow line has a pressure detector 77 which is in communication with the control means 21. Preferably, sample loop 35 has a pressure detector 79 in communication with the control means allowing the control means 21 to compare values and control pressure source 37 to match the operating pressure. In the alternative, the control means 21 can be set with predetermined values based on volumes or pressures to raise the pressure of the sample loop 35 to 75 to 125% of the operating pressure of the pump 13 as the sample 61 is held statically in sample loop 35. For example, the post-compression volume is preferably, 85 to 95% of the pre-compression volume.

Returning now to valve means 29a, 29b and 55', first valve 29a, in the first position, one of the first loop port 45 and the second loop port 47 is in fluid communication with the sample port 41 and the remaining first loop port 45 and second loop port 47 is in fluid communication with the withdrawal port 43. And, in the first position, the constant flow port 51 is in communication with the column port 49.

Second valve 29b and/or needle positioning means 55' is capable of assuming the second position. In the second position, at least one of the first loop port 45 and the second loop port 47 is in fluid communication with the pressure source, syringe pump 37 or 37'.

In the third position, the first loop port 45 and said second loop port 47 are in fluid communication with the constant flow port 51 and the column port 49. The valve means 29a and 29b are in signal communication with control means 21. The valve means 29a and 29b assume the first position upon receiving a first signal, assumes the second position upon receiving a second signal command and assumes the third position upon receiving a third signal command. Although referred to as a command signal, those skilled in the art will recognize that the command signal may comprise a series of instructions to effect an operation.

The sample introduction line 31 is in fluid communication with the sample port 41 and with a source of sample. The source of sample may take several forms. Typically, as depicted in FIG. 2, the source of sample is a needle 55. Needle 55 is robotically controlled by control means 21. The needle 55 is used to descend into a sample vial 57 where sample is withdrawn. Typically, the sample injector device 15 would have a plurality of vials 57 and the needle 55 would move from vial to vial.

As depicted in FIG. 2, a second valve is labeled with the numeric designation 29b. Second valve 29b has two positions, one in which the sample receiving line 31 is in communication with sample and a second position in which the valve assumes the second position previously described.

In the alternative, as depicted by dotted lines, the needle 55 can be used in the sense of a valve to redirect the sample introduction line 31 robotically to the pressure source 37 to which such needle 55 is placed in fluid communication. Thus, the needle 55 has two positions. In one position, the needle 55 is placed in a sample vial 57 and upon the withdrawal pump 36 depressurizing the sample introduction line 31, sample is drawn up into such line. In the second position, needle, designated now by the numeral 55' to denote the second position, is placed in fluid communication with the pressure source, syringe pump 37' to pressurize the sample and fluids in the sample loop 35.

The control means 21 is in signal communication with the pressure source 37, the withdrawal pump 36 and the valve means, first valve 29a and second valve 29b or needle movement means as represented by needle 55'. The control means instructs by issuing a first command signal to the valve means 29a and 29b or 55' to assume the first position in which a sample is received in the sample introduction line. The control means issues a second command signal to the valve means 29b, 29b and/or 55' to assume the second position and signaling the pressure source 37 or 37' to pressurize the sample loop 35 while the sample is received therein to 70 to 100% of the system pressure to reduce pressure perturbations as the valve means moves to the third position.

The operation of the invention will be described with respect to the method of the present invention for placing a sample in a chromatography system having a system pressure. The method comprises the steps of providing a device 15 having a valve means 29a, 29b or 55', a sample introduction line 31, a withdrawal line 33, a sample loop 35, a column line 23b, a constant flow line 23a, a withdrawal pump 36, a pressure source 37, and a control means 21, as previously described. The device 15 is operated or programmed to operate to place sample in the sample loop 35 under pressure from said pressure source 37 or 37' at 70% to 100% of the system pressure prior to placing the valve means 29a in the third position to reduce pressure perturbations.

Thus, embodiments of the present invention have been described with respect to methods and devices for placing a sample in a chromatographic system with the understanding that the description has been directed to preferred embodiments which are capable of modification and alteration without departing from the teaching and disclosure herein. Therefore, the invention should not be limited to the precise details set forth herein but should include such subject matter as set forth in the claims that follow and their equivalents.

What is claimed is:

1. A device for placing a sample in a chromatography system having a system pressure at which solvent flows, the device comprising:
   a valve means for selectively placing a sample in a column line comprising a sample port, withdrawing port, first loop port, second loop port, column port and constant flow port; said valve means having a plurality of positions comprising a first position in which said one of said first loop port and said second loop port is in communication with said sample port and the remaining first loop port and second loop port is in communication with said withdrawal port, and said constant port is in communication with said column port, a second position in which at least one of said first loop port and said second loop port is in fluid communication with a pressure source, and a third position in which said first loop port and said second loop port are in fluid communication with said constant flow port and said column port; said valve means in signal communication with control means and assuming said first position upon receiving a first signal command, assuming said second position upon receiving a second signal command and assuming said third position upon receiving a third signal command;
   a sample introduction line in fluid communication with said sample port and with a source of sample and, upon said valve means assuming a second position, a source of pressure, said sample introduction line for receiving sample and conveying said sample into said valve means and through at least one of said first sample port and second sample port and into a sample loop when said valve means is in said first position and pressurizing said sample in said sample loop upon said valve means assuming said second position;
   a withdrawal line in fluid communication with said withdrawal port and a source of reduced pressure to withdraw sample through said sample introduction line and into valve means and said sample loop upon said valve means assuming said first position;
   a sample loop in fluid communication with said first sample port and said second sample port for receiving sample withdrawn through said valve means and holding said sample, and upon said valve means assuming said second position, pressurizing said sample, and upon said valve means assuming a third position, discharging said pressurized sample through said valve means and said column port as said sample loop is placed in communication with said constant flow port and said column port;
   a column line in fluid communication with said column port for receiving sample from said sample loop and for directing sample to one or more columns;
   a constant flow port for being placed in communication with a source of the solvent;
   a withdrawal pump in fluid communication with said withdrawal line and in signal communication with control means, said withdrawal pump depressurizing said withdrawal line to pull sample into said sample introduction line in said first position;
   a pressure source in fluid communication with at least one of said sample introduction line and said sample loop for placing said sample in said sample loop under pressure; and,
   a control means in signal communication with said pressure source, said withdrawal pump and said valve means, said control means instructing said valve means to assume said first position in which a sample is received in said sample introduction, said control means issuing said valve means to assume said second position and signaling said pressure source to pressurize said sample loop while said sample is received therein to 70 to 100% of the system pressure to reduce pressure perturbations when said valve means moves to said third position and introduces the pressurized sample to the solvent flowing at the system pressure.

2. The device of claim 1 wherein said sample has a trailing end and a lead front, said sample having at least one air bubble at least at one of said trailing end and said lead front.

3. The device of claim 2 wherein said sample introduction line has a needle which descends into a sample vial.

4. The device of claim 3 wherein said needle is movable between a position in communication with a sample vial and a position in fluid communication with said pressure source.

5. The device of claim 1 wherein said pressure source is in fluid communication with said sample introduction line during pressurization.

6. The device of claim 1 wherein said sample loop has a volume in the range of 0.5 to 50 microliters.

7. The device of claim 6 wherein said sample has a volume of 0.1 to 45 microliters.

8. The device of claim 1 wherein said sample has a precompression volume and a post compression volume, said post compression volume is 85 to 95% of the precompression volume.

9. The device of claim 1 wherein said pressure source places said sample loop under pressure by changing volume at the rate of approximately 10 to 800 microliters per minute.

10. The device of claim 1 further comprising a chromatography pump said chromatography pump in fluid communication with a pump line.

11. The device of claim 1 further comprising a column, said column in fluid communication with said column line.

12. The device of claim 1 further comprising a detector said detector in fluid communication with said column.

13. The device of claim 1 wherein said sample is placed under pressure in said sample loop under static conditions.

14. A method of a placing a sample in a chromatography system having a system pressure at which solvent flows, the chromatography system comprising a device having a valve means, a sample introduction line, a withdrawal line, a sample loop, a column line, a constant flow line a withdrawal pump, a pressure source, and a control means; said valve means for selectively placing sample in said column line comprising a sample port, withdrawing port, first loop port, second loop port, column port and constant flow port; said valve means having a plurality of positions comprising a first position in which said one of said first loop port and said second loop port is in communication with said sample port and the remaining first loop port and second loop port is in communication with said withdrawal port, and said constant port is in communication with said column port, a second position in which at least one of said first loop port and said second loop port is in fluid communication with a pressure source, and a third position in which said first loop port and said second loop port are in fluid communication with said constant flow port and said column port; said valve means in signal communication with control means and assuming said first position upon receiving a first signal command, assuming said second position upon receiving a second signal command and assuming said third position upon receiving a third signal command; said sample introduction line in fluid communication with said sample port and with a source of sample and, upon said valve means assuming a second position, a source of pressure, said sample introduction line for receiving sample and conveying said sample into said valve means and through at least one of said first sample port and second sample port and into said sample loop when said valve means is in said first position and pressurizing said sample in said sample loop upon said valve means assuming said second position; said withdrawal line in fluid communication with said withdrawal port and a source of reduced pressure to withdraw sample through said sample introduction line and into valve means and said sample loop upon said valve means assuming said first position; said sample loop in fluid communication with said first sample port and said second sample port for receiving sample withdrawn through said valve means and holding said sample, and upon said valve means assuming said second position, pressurizing said sample, and upon said valve means assuming a third position, discharging said pressurized sample through said valve means and said column port as said sample loop is placed in communication with said constant flow port and said column port; said column line in fluid communication with said column port for receiving sample from said sample loop and for directing sample to one or more columns; said constant flow line in fluid communication with said constant flow port and for being placed in communication with a source of solvent; said withdrawal pump in fluid communication with said withdrawal line and in signal communication with control means, said withdrawal pump depressurizing said withdrawal line to pull sample into said sample introduction fine in said first position; said pressure source in fluid communication with at least one of said sample introduction line and said sample loop for placing said sample in said sample loop under pressure; and, said control means in signal communication with said pressure source, said withdrawal pump and said valve means, said control means instructing said valve means to assume said first position in which a sample is received in said sample introduction, said control means issuing said valve means to assume said second position and signaling said pressure source to pressurize said sample loop while said sample is received therein to 70 to 100% of the system pressure to reduce pressure perturbations as said valve means moves to said third position, the method comprising the steps of:
providing the device; and
operating said valve means to assume said second position to place the sample in said sample loop under pressure from said pressure source at 70% to 100% of the system pressure and thereby to reduce pressure perturbations when said valve means moves to said third position and introduces the pressurized sample to the solvent flowing at the system pressure.

15. The method of claim 14 wherein said sample has a trailing end and a lead front, said sample having at least one air bubble at least one of said trailing end and said lead front.

16. The method of claim 15 wherein said sample introduction line has a needle which descends into a sample vial.

17. The method of claim 16 wherein said needle is movable between a position in communication with a sample vial and a position in fluid communication with said pressure source.

18. The method of claim 14 wherein said pressure source is in fluid communication with said sample introduction line during pressurization.

19. The method of claim 14 wherein said sample loop has a volume in the range of 0.5 to 50 microliters.

20. The method of claim 14 wherein said sample has a volume of 0.1 to 45 microliters.

21. The method of claim 14 wherein said sample has a precompression volume and a post compression volume, said post compression volume is 85 to 95% of the precompression volume.

22. The method of claim 14 wherein said pressure source places said sample loop under pressure by changing volume at the rate of approximately 10 to 800 microliters per minute.

23. The method of claim 14 further comprising a chromatography pump, said chromatography pump in fluid communication with a pump line.

24. The method of claim 14 further comprising a column, said column in fluid communication with said column line.

25. The method of claim 14 further comprising a detector said detector in fluid communication with said column.

26. The method of claim 14 wherein said sample is placed under pressure in said sample loop under static conditions.

27. A liquid chromatography system comprising:
a pump moving a flow of solvent at a system pressure;
a sample loop holding a sample pressurized to at least 70% of the system pressure;
valve means coupled to the sample loop that holds the pressurized sample; and
control means operating the valve means to place the pressurized sample in the sample loop into the flow of the solvent being moved by the pump at the system pressure.

28. In a chromatography system having a system pressure, a method of introducing a sample to a flow of solvent, the method comprising:
pumping the flow of solvent at the system pressure;
pressurizing the sample in a sample loop of the chromatography system to at least 70% of the system pressure in order to produce a pressurized sample before introduction of the sample to the flow of solvent; and
introducing the pressurized sample into the flow of the solvent being pumped at the system pressure.

* * * * *